United States Patent
Lutri et al.

(10) Patent No.: US 7,122,712 B2
(45) Date of Patent: Oct. 17, 2006

(54) SURGICAL BANDAGE AND METHODS FOR TREATING OPEN WOUNDS

(76) Inventors: Thomas P. Lutri, 550 NE. 21st Ave., Deerfield Beach, FL (US) 33441; John C. Bush, Jr., 550 NE. 21st Ave., Deerfield Beach, FL (US) 33441

( * ) Notice: Subject to any disclaimer, the term of this patent is extended or adjusted under 35 U.S.C. 154(b) by 0 days.

(21) Appl. No.: 10/392,143

(22) Filed: Mar. 19, 2003

(65) Prior Publication Data

US 2004/0106888 A1    Jun. 3, 2004

Related U.S. Application Data

(60) Provisional application No. 60/430,257, filed on Dec. 2, 2002.

(51) Int. Cl.
  *A61F 13/00* (2006.01)
  *A61F 15/00* (2006.01)
(52) U.S. Cl. .............. 602/43; 602/53; 602/54; 602/58
(58) Field of Classification Search ........ 606/213–216; 602/41–59; 604/304–308; 128/888, 889
See application file for complete search history.

(56) References Cited

U.S. PATENT DOCUMENTS

| | | | |
|---|---|---|---|
| 114,750 A * | 5/1871 | Battersby .............. 606/215 |
| 363,538 A | 5/1887 | Penny | |
| 1,230,445 A * | 6/1917 | Tweed ................. 606/215 |
| 1,774,489 A | 8/1930 | Sarason | |
| 2,196,296 A | 4/1940 | Flynn | |
| 2,751,909 A * | 6/1956 | Weitzner ............... 606/215 |
| 3,698,395 A | 10/1972 | Hasson | |
| 3,971,384 A | 7/1976 | Hasson | |
| 3,991,754 A | 11/1976 | Gertzman | |
| 4,423,731 A | 1/1984 | Roomi | |
| 4,447,482 A | 5/1984 | Heinzelman et al. | |
| RE31,887 E | 5/1985 | Hodgson | |
| 4,526,166 A * | 7/1985 | Silber ................... 602/58 |
| 4,612,230 A | 9/1986 | Liland et al. | |
| 4,646,731 A | 3/1987 | Brower | |

(Continued)

FOREIGN PATENT DOCUMENTS

GB        319215        11/1930

OTHER PUBLICATIONS

Copy of the International Search Report.

*Primary Examiner*—Henry Bennett
*Assistant Examiner*—Kari Petrik
(74) *Attorney, Agent, or Firm*—James J. Lillie; Lillie Law, LLC

(57) ABSTRACT

A surgical bandage for treating a wound that allows various fluids or fluid-like substances including cyanoacrylate adhesives to be applied. The surgical bandage has a wound treatment portion for being placed over a wound and a place for a flowable cyanoacrylate adhesive or any other fluid or fluid-like substance to be applied to the underlying wound (laceration, surgical incision or other tissue separation). A source is used to apply the cyanoacrylate or other fluid to the wound treatment portion flowing through at least one opening of the wound treatment portion to the underlying wound and its surrounding area either by direct application or from a non-contact distance. The surgical bandage allows for direct visualization before, during and after its application. The surgical bandage allows for removal of blood or any fluid that may be present in, on or around the wound by blotting or wiping.

10 Claims, 3 Drawing Sheets

U.S. PATENT DOCUMENTS

| | | |
|---|---|---|
| 4,780,168 A | 10/1988 | Beisang et al. |
| 4,865,026 A | 9/1989 | Barrett |
| 4,881,546 A | 11/1989 | Kaessmann |
| 4,899,762 A | 2/1990 | Muller |
| 4,950,282 A | 8/1990 | Beisang et al. |
| 4,999,235 A | 3/1991 | Lunn et al. |
| 5,009,663 A | 4/1991 | Broome |
| 5,047,047 A | 9/1991 | Yoon |
| 5,176,703 A | 1/1993 | Peterson |
| 5,259,835 A | 11/1993 | Clark et al. |
| 5,437,623 A * | 8/1995 | McClees et al. .............. 602/59 |
| 5,445,597 A | 8/1995 | Clark et al. |
| 5,456,660 A | 10/1995 | Reich et al. |
| 5,780,048 A | 7/1998 | Lee |
| 5,902,443 A | 5/1999 | Kanakubo et al. |
| 6,042,599 A | 3/2000 | Huttner et al. |
| 6,124,521 A | 9/2000 | Roberts |
| 6,155,265 A | 12/2000 | Hammerslag |
| 6,355,858 B1 | 3/2002 | Gibbins |
| 6,386,203 B1 | 5/2002 | Hammerslag |
| 6,596,917 B1 | 7/2003 | Oyaski |
| 2002/0099315 A1 | 7/2002 | Lebner |
| 2002/0193721 A1 * | 12/2002 | VanDruff .................... 602/41 |
| 2003/0032901 A1 | 2/2003 | Oyaski |
| 2003/0050590 A1 | 3/2003 | Kirsch |
| 2003/0153861 A1 | 8/2003 | Royer |
| 2005/0015036 A1 * | 1/2005 | Lutri et al. .................. 602/41 |

* cited by examiner

SURGICAL BANDAGE AND METHODS FOR TREATING OPEN WOUNDS

PRIORITY

This application claims priority from a United States Provisional Application filed on Dec. 2, 2002 and assigned U.S. Provisional Application Ser. No. 60/430,257, the contents of which are incorporated herein by reference.

FIELD OF THE INVENTION

The present invention relates to surgical bandages, specifically to bandages that promote wound healing having both the means to approximate (or bring into apposition) the wound edges of a laceration or surgical incision under direct visualization and a means for directly applying medicines or other agents after the wound has been stabilized and closed. While the surgical bandage of the present invention holds the wound edges in close approximation, the structure of the surgical bandage allows substances, such as medicines (e.g., antibiotics, pain relieving medicines and agents that promote wound healing) and adhesives both so-called bio-adhesives (e.g. fibrin and other tissue sealants) and super glues (e.g. cyanoacrylates) to come directly into contact with the surface near the wound's edges. The thin structure of the inventive surgical bandage also allows for the use of ultrasound energy to promote wound healing. The features of the surgical bandage allow direct visualization of the wound edges before, during and after the approximation of the wound edges and the process of application of the surgical bandage. Direct visualization of the wound area after application of a fluid or fluid like substance is possible provided that the fluid or fluid like substance is not opaque.

BACKGROUND OF THE INVENTION

In the past many methods have been developed to bring into apposition the edges of a wound or surgical incision so that the natural process of wound healing can occur. Among the products developed in the past that approximate wound edges include sutures made from various materials both naturally occurring and synthetic, many variations of tapes and metallic staples. All of these items involve methods that have advantages and disadvantages.

Sutures (or stitches) have the advantage of strength in holding the wound edges in close approximation but are somewhat complicated and time-consuming to place. Sutures also require a relatively high level of expertise and experience to use. Placement and removal of sutures may involve some pain and may require the use of local anesthetics. There is the inconvenience of a second visit to a healthcare professional which is usually required to remove the sutures.

Tape is simple and fast to use to approximate wound edges and requires little expertise and only minimal experience. However because the strength is dependent on adhesives that are pre-placed on the surface of the tape and are subject to losing their adhesive ability over time or with exposure to moisture, tape may not hold the wound edges close together for a long enough period of time to allow the natural wound healing process to occur.

Metallic staples have the advantage of strength in holding the wound edges close together but require expertise and experience to use them effectively. Like sutures, placement of staples may be painful and require the use of local anesthetics. Staples also involve the inconvenience of a second trip to have them removed by a healthcare professional. In addition, both sutures and staples may leave a scar pattern that is cosmetically unattractive.

Recently, adhesives have been developed to provide a way to bond wound edges in close approximation while the natural process of wound healing occurs. Products related to "super glue" or cyanoacrylates have been used to bond the wound edges together. The bond is formed when liquid cyanoacrylate is spread tangentially along the surfaces at the wound's edges spanning the edges. The liquid cyanoacrylate reacts with moisture on the surfaces and then hardens to form a solid mass that holds the wound edges together by bridging the edges together at their surfaces. It is important that the liquid cyanoacrylate not pass into the wound itself.

Techniques for the use of cyanoacrylates often involve having a healthcare professional apply the cyanoacrylate while holding the wound edges together with his gloved fingers or forceps. A total of 3–4 applications should be spread in layers directly over the junction of the tightly approximated wound edges allowing 10–15 seconds between applications for the liquid cyanoacrylate to set or harden. One recent article recommended that the total time that the wound edges should be held closely together is 2½ minutes. Also, it is critical that the wound edges be held in close approximation to ensure that none or a minimal amount of the adhesive enters the wound itself and is allowed to contact the structures under the skin. Further, holding the wound in close approximation also creates a better cosmetic result after healing has occurred (i.e., no scar or a less noticeable scar).

A device that will simplify the process and help healthcare professionals follow the proper procedure will ensure that these adhesives are used effectively. One patent describes a bandage having a porous bonding member or bonding pad that can be used in conjunction with a carrier member for wound apposition. However, the bonding pad is thick and therefore, has the disadvantage of not allowing direct visualization of the wound and the adjacent areas before, during and after its application.

SUMMARY OF THE INVENTION

The present invention provides a surgical bandage which facilitates closure, stabilization, and dressing of an open wound, laceration or surgical incision while making possible the subsequent application of medicines, agents, and ultrasonic energy (or other form of energy) which promote wound healing and/or adhesives through openings or interstices in the surgical bandage while allowing for visualization during and following placement of the surgical bandage and any subsequent application of any substances through its openings.

The central, non-absorbent segment of the surgical bandage of the present invention is thinner, allowing direct application and passage of substances through to the underlying surface. The thinness of the central segment also allows for substances to form a continuous layer that overlies the closed wound as they fill and overflow the openings of the central, non-absorbent segment. The surgical bandage of the present invention has been designed to allow for maximal direct visualization of the process of approximating the edges of the wound, laceration or surgical incision. The ability to visualize the wound surface, even after closure, is very important in monitoring the wound healing process to guard against infection and for other obvious reasons. Also, the openings in the surgical bandage allow an opportunity to wipe away or blot dry any blood, transudate or other form of liquid or moisture that may have accumulated near the approximated wound edges prior to direct application of any substance. Another possible benefit of the surgical bandage described herein is that wounds that occur in areas where there is increased tension on the skin because of repetitive flexion and extension at or near a joint can have the surgical bandage left in place after its placement to help prevent separation of the closed wound edges once they have been approximated and subsequent application of any substance.

The surgical bandage of the present invention can be used with many different substances including adhesives (such as cyanoacrylates) or other tissue sealants to provide for quick, easy and effective wound, laceration or surgical incision closure and stabilization after which the natural healing process can occur. It is contemplated that adhesives (such as cyanoacrylates) and other tissue sealants may be used together with the surgical bandage of the present invention, by individuals who are not healthcare professionals.

The present invention is a one-piece, thin surgical bandage that is comprised of three segments consisting of two thin solid pieces of tape on either end connected to a thin, central, non-absorbent segment in a linear fashion. The central segment may include a thin netting, thin parallel fibers, and/or a thin layer made from a transparent material with interstices of variable shapes and sizes. The lengths and widths of the individual segments vary to allow for different lengths and widths of the surgical bandage itself. Each individual surgical bandage unit can be packaged as a sterile, single use unit.

The segments at the ends of the surgical bandage are thin, solid pieces of tape that will have adhesive on one surface and no adhesive on the other. The adhesive side may have a separate protective layer that may be peeled away so that the thin, solid tape can be applied to an appropriate surface. The protective layer will prevent the tape from accidentally sticking to an unintended surface. The protective layer will also serve to help maintain the adhesiveness of the adhesive side of the tape. The solid tape may be made of various possible materials and may be transparent so that the surface that it is adherent to is made visible. Materials that are used in the solid tape should ideally be non-allergenic and non-irritating to humans and animals. Possible candidates for use in manufacturing the solid tape include thin plastic; polymers such as polyvinyl, polypropylene, polyurethane or polyester; fabrics (such as cotton, nylon, silk or other naturally occurring or synthetic fabrics) silicon or silicon coated material, latex or rubber, Teflon and Teflon related products, acetate products, Kevlar and paper, cellulose or fiber-based material. Moreover, the two thin solid pieces of tape do not allow for fluid to flow therethrough. Thus the two thin solid pieces of tape contain no internal cavities for fluids to flow therethrough.

An optional "pull string" string or thread-like device may be placed within or under the solid tape at the border where the solid tape meets the central segment to facilitate cutting, separating and removing the two solid tape ends from the central segment in a manner similar to the way a "pull-string" is used to open a FedEx™ envelope. This would enable the two pieces of solid tape to be removed after the central portion of netting, parallel fibers or thin layer with interstices has otherwise become secured to its underlying surface by a means to be described later.

The central, non-absorbent segment of netting, parallel fibers or thin layer with interstices may or may not have adhesive applied to one side. If adhesive is applied to one side then a protective layer as described above may or may not be present to function as described previously. The open spaces of the non-absorbent netting, non-absorbent parallel fibers or the interstices of the non-absorbent, thin layer shall be of sufficient size to allow medicines, agents that promote wound healing and/or adhesives to freely pass through the openings and establish direct contact with the underlying surface. The central segment of netting, parallel fibers or thin layer with interstices is very thin. The reason for this thinness will be explained below.

The openings will be designed of sufficient size, spatial arrangement and orientation to allow direct visualization of the underlying surface to occur prior to and during application and adhesion of the two tape segments at either end of the surgical bandage. Direct visualization is also possible prior to and after application of any agent that may pass through the openings of the central segment and after the central segment has been secured either being held in place by the two end segments of tape or possibly by another adhesive that was subsequently placed prior to the removal of the two tape end segments. To enhance direct visualization, the central segment may also be made from a thin layer of material that is transparent. Materials that are used to make the central segment of netting, parallel fibers or thin layer with interstices include the materials described above to make the tape segments and fibers or fiber-like materials that may or may not be coated with another substance such as resin, wax, silicon, plastic or other polymer, latex or other rubber, or other coating substance.

An example of a usage of this invention may be facilitating the closure of a gaping skin wound, laceration or surgical incision of a human or animal. Prior to using the surgical bandage, the wound, laceration or surgical incision will have been cleaned and debrided in manner consistent with accepted medical or veterinary practice. Hemostasis should already have been accomplished using generally accepted and established hemostasis methods. If necessary, any layered closure using subcutaneous or deep sutures should be done prior to use of the surgical bandage. The area around the wound, laceration or surgical incision should be made dry to ensure good adhesion of the surgical bandage. Immediately prior to placement of the surgical bandage a substance that may improve the adhesiveness of the surgical bandage such as tincture of benzoin may be applied to the surrounding skin.

One end segment of solid tape is prepared by removing the protective layer, if present, from the surface on which there is adhesive. This solid tape end segment is placed with the bare adhesive surface facing toward the skin surface adjacent to one side of the gaping wound, laceration or surgical incision and is pressed securely onto the skin surface so that adhesion occurs. Placement of the solid tape segment should be done so that the central segment of netting, parallel fibers or thin layer with interstices directly overlies and spans the gaping wound, laceration or surgical incision.

Once one side of the surgical bandage has been placed and is adherent, the protective layer, if present, should be removed from the other end segment of solid tape and the central segment of netting, parallel fibers or thin layer with interstices if adhesive was present. Using appropriate tension or traction, the apposing wound edges should be brought into close approximation by pulling on the end segment that has not yet been placed on or adhered to the skin surface. Because direct visualization is possible through the central segment, the alignment of the edges of the wound, laceration or surgical incision can be accomplished in an optimal manner.

Once the alignment is optimal or acceptable, the free solid tape end segment is placed and pressed onto the skin surface on the other side of the wound, laceration or surgical incision. At this point the gap that was previously present in the wound, laceration or surgical incision should be significantly reduced or absent and the edges of the wound, laceration or surgical incision should be held securely together in close approximation by the surgical bandage. One option at this point would be to plan to leave the surgical bandage in place for a desired period of time so that the wound, laceration or surgical incision would heal with its edges well approximated.

A medicine (such as an antibiotic or anesthetic) or an agent to promote wound healing could be applied at this time. The healing of the wound, laceration or surgical incision could be closely monitored and additional medicine or agent to promote wound healing could be applied as needed. Another option after the edges of the wound, laceration or surgical incision are securely held together in close approximation is to apply an adhesive. One possible adhesive is a cyanoacrylate. Because the wound is now stabilized in a position with wound edges closely approximated, a cyanoacrylate or other adhesive can easily be applied to the appropriate areas using direct visualization.

Because the central segment is very thin, the openings in the netting, parallel fibers of thin layer with interstices form shallow wells that can easily fill with the liquid cyanoacrylate and overflow into adjacent openings so that one continuous layer of cyanoacrylate will be formed. In order to form one continuous layer of hardened cyanoacrylate, the viscosity of the cyanoacrylate may or may not need to be increased. Once the recommended amount of adhesive has been applied and sufficient time has elapsed to allow the adhesive to harden or set, the two end segments of solid tape can be removed using the "pull-string" previously described to separate the solid tape from the central gauze segment. This will leave the central gauze segment which has become enveloped by the hardened adhesive attached to the skin where it will remain until the hardened adhesive and central gauze, both slough off together or otherwise become detached from the skin surface. This sloughing off the combined hardened adhesive and central gauze segment will occur several days later after the natural healing process has taken place.

DETAILED DESCRIPTION OF THE INVENTION

Figure 1:
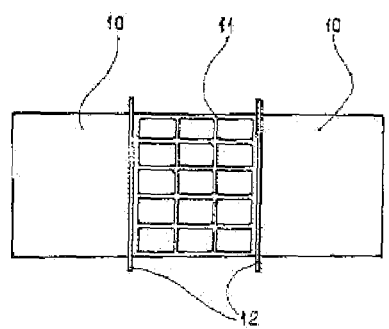
FIG. 1 is a top view of the surgical bandage showing the three segments of the surgical bandage and the placement of the optional "pull-string" type devices.

FIG. 1 is a top view of one embodiment of a surgical bandage according to the present invention. The surgical bandage is preferably packaged in a sterile condition within a package and distributed as a single-use surgical bandage.

Figure 2:
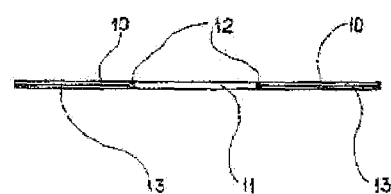
FIG. 2 is a side view of the surgical bandage showing the three segments of the surgical bandage and the optional thin protective layer attached to the adhesive side of the surgical bandage.

The surgical bandage includes two solid tape end segments 10, a central, non-absorbent segment of netting 11 and two "pull strings"12. FIG. 2 is a side view of the surgical bandage shown in FIG. 1 that shows the two end segments of solid tape 10, the central segment of netting 11, the "pull strings"12 and the protective layer that covers the adhesive side of the solid tape segments and the adhesive side of the central segment of netting 11. Even though FIG. 1 shows netting 11, alternatively, the netting 11 could be replaced with parallel fibers (see FIG. 9) or a thin layer with interstices (see FIG. 10). That is, the netting 11 could be replaced with any type of lattice structure.

Figure 3:
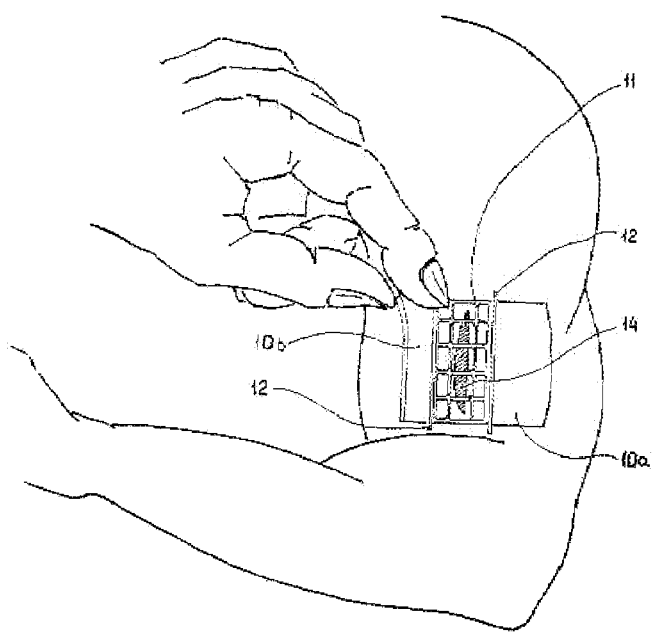
FIG. 3 is a top view of a representation of a gaping skin laceration showing that one of the solid tape segments has already been pressed against the skin surface and is adhering to one side of the wound.
Figure 4:
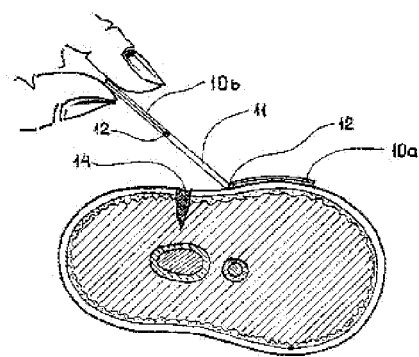
FIG. 4 is a cross-sectional view showing the gaping skin laceration with one of the solid tape segments already adhering to the skin surface on one side of the laceration.

A visual demonstration of the use of the surgical bandage is shown in FIGS. 3 through 8. FIG. 3 is a top view of a skin surface that has a laceration 14. In FIG. 3 one end segment of solid tape 10a has had its protective layer 13 removed, and the solid tape segment 10a has been pressed onto the skin surface on one side of a laceration 14. The solid tape segment 10a is adhering firmly to the skin surface in FIG. 3. FIG. 4 shows the same representation shown in FIG. 3.

In FIG. 4 the laceration 14 is shown to be gaping with the solid tape segment 10a adhering to the skin surface adjacent to one of the edges of the laceration 14. In FIG. 4 the solid tape segment 10b has had its protective layer removed. The solid tape segment 10b is being grasped by the person applying the surgical dressing and is being held above the skin surface.

Figure 5:
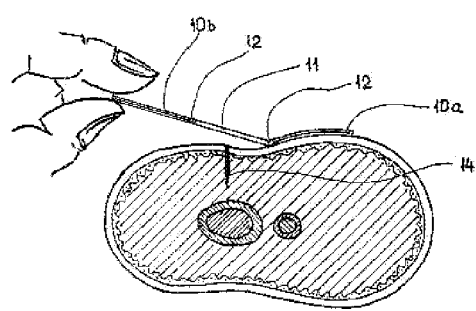
FIG. 5 is a cross-sectional view of the laceration with the gap of the laceration being reduced when traction or tension is used by pulling on the free, unattached solid tape end segment while the other solid tape end segment is adhering to one side of the laceration.

FIG. 5 shows that one end segment of solid tape 10a is firmly adherent to one side of the laceration 14, and the person applying the surgical bandage is pulling or using traction on the unattached end segment of solid tape 10b. In FIG. 5, the tension or traction applied to the unattached solid tape segment 10b has caused the wound edges of the laceration 14 to come together and be closely approximated.

Figure 6:
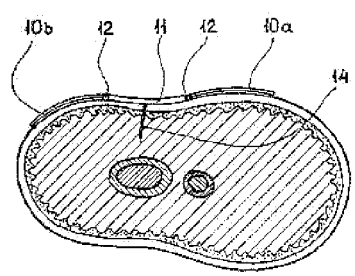
FIG. 6 is a cross-sectional view of the laceration after the gap of the laceration was reduced and both of the solid tape end segments have adhered to the surfaces on either side of the laceration.

FIG. 6 shows that both end segments of solid tape 10a, 10b have been pressed against and are adherent to the skin surface adjacent to the closely approximated laceration 14. In FIG. 6, the central, non-absorbent segment of netting 111 is positioned against and spans the laceration 14.

Figure 7:
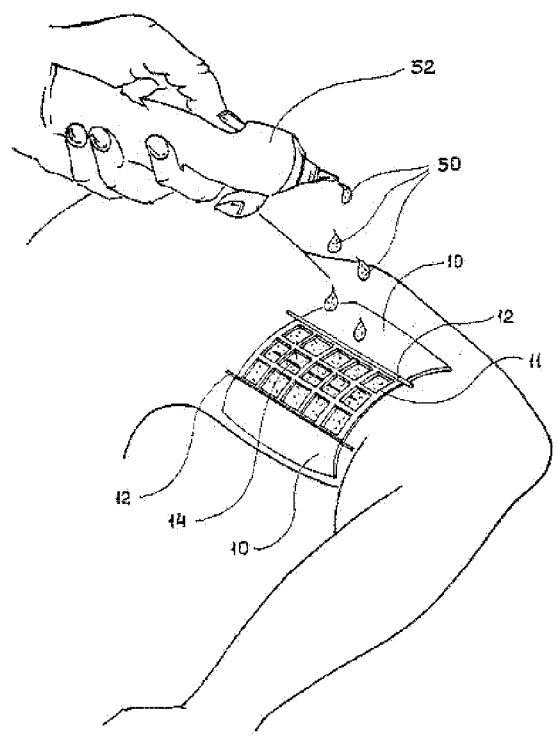
FIG. 7 is a top view of the laceration after the edges of the laceration have been closely approximated and both of the solid tape end segments have been pressed onto and are adhering to the skin surfaces on either side of the laceration.

FIG. 7 shows the same representation in FIG. 6. In FIG. 7 the surgical dressing has been positioned on the skin surface, and the end segments of the solid tape, 10a, 10b are adhering to the skin surface on either side adjacent to the closely approximated laceration 14. The central segment of netting 11 is positioned against and spans the closely approximated laceration 14. The representations of the surgical bandage in FIG. 6 and FIG. 7 show the desired position for applying medicines, agents that promote wound healing or adhesives.

Figure 8:
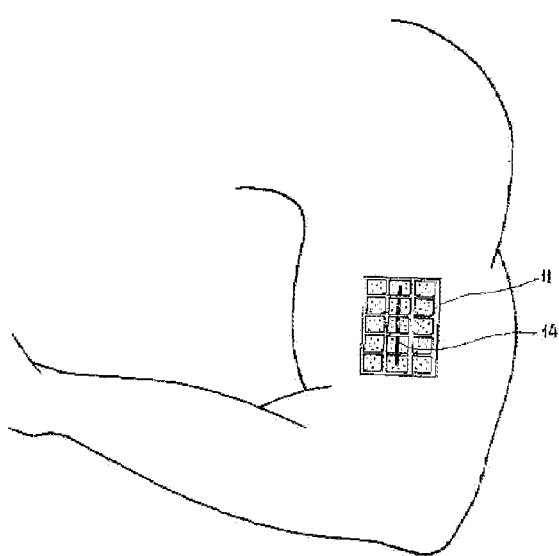
FIG. 8 is a top view of the laceration after a cyanoacrylate has been applied and has hardened and the two solid tape end segments have been removed using the "pull strings" to separate them from the central segment of netting.

FIG. 8 shows the closely approximated laceration 14 covered by the central, non-absorbent segment of netting 11 adhering to the skin surface edges adjacent to the laceration 14. In FIG. 8 a fluid 50 from a fluid source 52 is applied and allowed to harden, covering and enveloping the central, non-absorbent segment of netting 11. The fluid 50 is selected from the group consisting of medicaments, antibiotics, adhesives, saline and a combination thereof. Preferably, the fluid 50 is an adhesive, such as cyanoacrylate. FIG. 8 shows the surgical dressing after the two end segments of solid tape (10 in the previous figures) have been separated from the central segment of netting using the "pull strings" 12.

Figure 9:
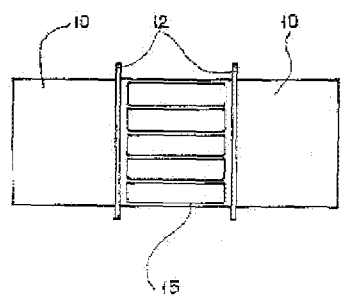
FIG. 9 is a top view showing another embodiment of the surgical bandage and showing the three segments of the surgical bandage and the placement of the optional "pull-string" type devices.

FIG. 9 shows two end segments of solid tape 10 on either side of a central segment of parallel fibers 15. Two "pull strings" 12 are positioned near the junction of the end segments of solid tape 10 and the central segment of parallel fibers 15. The "pull strings" 12 can be used to separate the end segments of solid tape 10 from the central segment of parallel fibers 15 after the central segment has been securely adhered to a surface by an adhesive.

Figure 10:
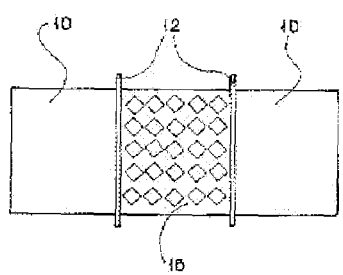
FIG. 10 is a top view showing still another embodiment of the surgical bandage and showing the three segments of the surgical bandage and the placement of the optional "pull-string" type devices.

FIG. 10 shows two end segments of solid tape 10 on either side of a central segment made from a thin layer of a transparent material with interstices 16. Two "pull strings" 12 are positioned near the junction of the end segments of solid tape 10 and the central segment of a thin layer with interstices 16. The "pull strings" 12 can be used to separate the end segments of solid tape 10 from the central segment of a thin layer with interstices 16 after the central segment has been securely adhered to a surface by an adhesive.

Preferably, the present invention is distributed as a wound treatment kit having at least one bandage packaged in a sterile condition and the fluid source 52 as shown by FIG. 8.

The described embodiments of the present invention are intended to be illustrative rather than restrictive, and are not intended to represent every embodiment of the present invention. Various modifications and variations can be made without departing from the spirit or scope of the invention as set forth in the following claims both literally and in equivalents recognized in law.

What is claimed is:

1. A surgical bandage for treating an open wound, said surgical bandage comprising:
   a netting member having a plurality of openings for permitting two way passage of fluids through the surgical bandage, wherein the plurality of openings provide for visualization of the wound; and
   at least two members connected to the netting member and being coplanar with the netting member, the at least two members having means for substantially closing the open wound by applying a force to at least one edge of the open wound means for securing the netting member over the closed wound, wherein the plurality of openings permit blood and other fluids from the wound to flow through the surgical bandage, and wherein fluid applied from one side of the netting member opposite the wound flows through the plurality of openings and directly contacts the closed wound and surrounding areas on the other side of the netting member, wherein said bandage further comprises means for detaching the at least two members by the use of pull strings placed adjacent to the netting member.

2. The surgical bandage of claim 1, wherein the netting member has an adhesive on at least one side.

3. The surgical bandage of claim 1, wherein the netting member includes a transparent material.

4. The surgical bandage of claim 1, wherein the plurality of openings provide for direct visualization of the wound before, during, and after closure.

5. The surgical bandage of claim 1, wherein the fluid is selected from the group consisting of: a gel, lotion, adhesive, cyanoacrylate, tissue sealant, cream, ointment, fibrin, fibrin-like substance, medicament, anesthetic, antibiotic, wound healing agent, and combinations thereof.

6. The surgical bandage of claim 1, wherein the netting member is nonabsorbent.

7. The surgical bandage of claim 1, wherein the netting member includes a lattice structure.

8. The surgical bandage of claim 1, wherein the fluid is applied from a substantially non-contact distance.

9. The surgical bandage of claim 1, wherein means for securing includes a pre-applied adhesive.

10. The surgical bandage of claim 1, wherein the netting member is adaptable for contouring to the patient's skin.

* * * * *